(12) United States Patent
Cole et al.

(10) Patent No.: US 11,058,414 B1
(45) Date of Patent: Jul. 13, 2021

(54) METHODS OF TISSUE REPAIR WITH DIRECT PASS CINCH

(71) Applicant: Arthrex, Inc., Naples, FL (US)

(72) Inventors: Brian J. Cole, Chicago, IL (US); Peter J. Dreyfuss, Naples, FL (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 17/136,641

(22) Filed: Dec. 29, 2020

(51) Int. Cl.
*A61B 17/04* (2006.01)
(52) U.S. Cl.
CPC ...... *A61B 17/0469* (2013.01); *A61B 17/0485* (2013.01); *A61B 17/0482* (2013.01)
(58) Field of Classification Search
CPC ............ A61B 17/0469; A61B 17/0485; A61B 17/0482; A61B 2017/06052
See application file for complete search history.

(56) References Cited

U.S. PATENT DOCUMENTS

| | | | | |
|---|---|---|---|---|
| 5,129,912 A * | 7/1992 | Noda | ................. | A61B 17/0469 289/1.2 |
| 5,207,694 A * | 5/1993 | Broome | ........... | A61B 17/12013 24/16 PB |
| 5,681,333 A * | 10/1997 | Burkhart | ............ | A61B 17/0469 128/898 |
| 5,895,395 A * | 4/1999 | Yeung | ................. | A61B 17/0469 606/144 |
| 6,629,984 B1 * | 10/2003 | Chan | ................. | A61B 17/0482 606/139 |
| 9,398,906 B2 | 7/2016 | Stone et al. | | |
| 2005/0033365 A1 * | 2/2005 | Courage | .......... | A61B 17/06109 606/232 |
| 2009/0036905 A1 | 2/2009 | Schmieding | | |
| 2010/0198235 A1 * | 8/2010 | Pierce | ................ | A61B 17/0483 606/148 |
| 2012/0277770 A1 * | 11/2012 | Fenton | ............... | A61B 17/0487 606/151 |
| 2016/0199057 A1 * | 7/2016 | Parsons | .............. | A61B 17/0485 606/144 |
| 2020/0069306 A1 * | 3/2020 | Nikolavsky | ........ | A61B 17/0491 |

OTHER PUBLICATIONS

Liodakis et al., "The lasso-loop, lasso-mattress and simple-cinch stitch for arthroscopic rotator cuff repair: are there biomechanical differences?" Arthroscopy and Sports Medicine, Aug. 2016, vol. 136, pp. 1581-1585, Springer Nature, London, United Kingdom.
Parnes et al., "The oblique Mattress Lasso-Loop Stitch for Arthroscopic Capsulolabral Repair," Arthroscopy Techniques, Oct. 2016, vol. 5(5), pp. e959-e963, Elsevier, Amsterdam, Netherlands.
Unknown, "CHIA PERCPASSER Suture Passer, Surgical Technique," DePuy Synthes—Mitek Sports Medicine, 2017, pp. 1-4, Raynham, Massachusetts.
Unknown, "Shoulder Labrum Portfolio," Zimmer Biomet, Sep. 2019, 11 pages, Warsaw, Indiana.
Unknown, "Shoulder Restoration System," ConMed Corporation, 2016, Revision 1, 20 pages, Utica, New York.

* cited by examiner

*Primary Examiner* — Dianne Dornbusch
(74) *Attorney, Agent, or Firm* — Potomac Law Group PLLC

(57) ABSTRACT

Methods for tissue repairs with direct pass cinch are disclosed. A direct pass cinch is created with a suturing construct using only one portal and without shuttling steps. The suturing construct may be a loop terminating in a single tail.

9 Claims, 2 Drawing Sheets

METHODS OF TISSUE REPAIR WITH DIRECT PASS CINCH

FIELD OF THE INVENTION

The disclosure relates to the field of surgery and, more specifically, to methods of passing suture.

BACKGROUND

Arthroscopic suturing techniques and instruments have been developed to facilitate suturing of tissue during arthroscopic surgical procedures. In arthroscopic surgery, access to a surgical work site within a patient's body is normally provided through one or more portals formed directly in the patient's body, or through one or more cannulas inserted into the patient's body through small incisions. A chosen surgical procedure is carried out by a surgeon through the use of elongated instruments inserted through these cannulas and it often becomes necessary to suture selected tissue at the surgical work site.

Since the work site is only accessible through a small portal or cannula, and since it is very difficult to tie sutures within the body, various devices and techniques have been developed to enable the surgeon to tie and manipulate sutures arthroscopically. For example, some procedures enable the surgeon to pass suture material through selected tissue, form a surgical knot extracorporeally and then move the knot with a knot pusher through the portal or cannula into position adjacent the desired tissue to be sutured. Other instruments for passing suture, such as the SutureLasso™ device, sold by Arthrex, Inc. of Naples, Fla., incorporate a hollow needle for piercing tissue, and a wire loop insertable through the needle for retrieving suture. Yet other instruments such as Arthrex's Loop 'N' Tack passer allow for a knotless biceps tenodesis technique using the Loop 'N' Tack stitch configuration.

It would be desirable to provide instrumentation and methods of passing suture and forming a cinch stich with a single arthroscopic portal and without additional shuttling instruments such as graspers and knot pushers.

SUMMARY

Methods for surgical repairs are disclosed. A direct pass cinch is created with a suturing construct using only one portal and without shuttling steps. The suturing construct may be a loop terminating in a single tail.

Methods of passing suture are also disclosed. A first portion of a flexible strand is passed through soft tissue while a second portion of the flexible strand is passed around the soft tissue, using only one portal and without shuttling steps and additional instrumentation, in a single direct passing step.

DETAILED DESCRIPTION

Figure 1:
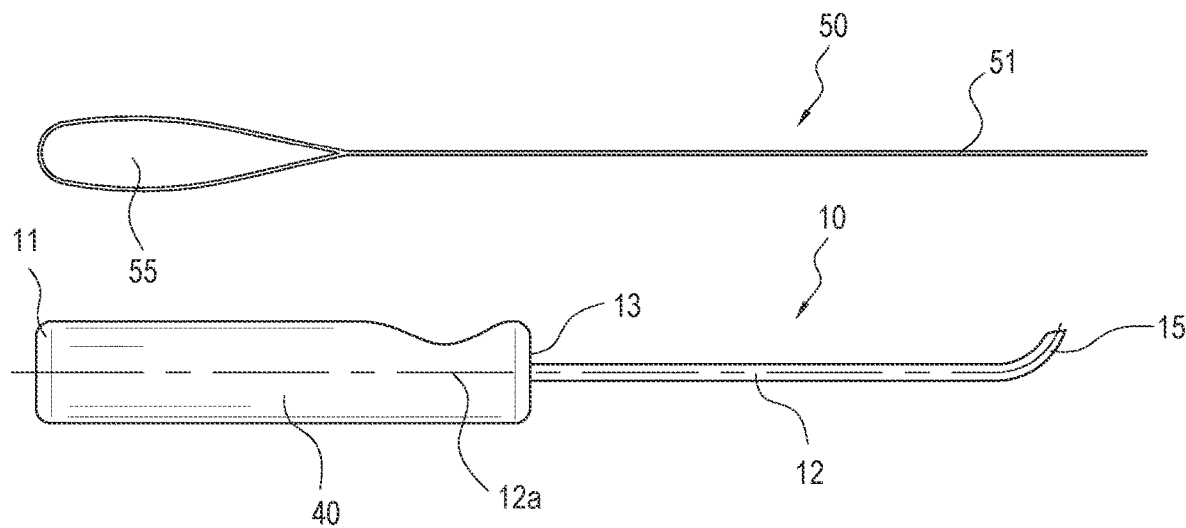
FIG. 1 illustrates a suture passing instrument and a suturing construct employed in a direct pass cinch tissue repair according to an exemplary embodiment.

The disclosure provides techniques for surgical repairs such as endoscopic surgical repairs (for example, arthroscopic surgeries). A first portion of a flexible construct is passed through a suture passer and through the tissue, the suture passer is removed, and the first portion of the flexible construct is passed through a second portion of the same flexible construct around the same tissue, to form a direct pass cinch. The flexible construct may be a suture loop terminating in a single tail. In an embodiment, the tissue can be soft tissue such as tendon or ligament. In an embodiment, the tissue can be a capsule. A suture passer can facilitate suture placement in soft tissue and formation of a Loop 'N' Tack™ stitch through a single arthroscopic portal and without shuttling steps.

A suture passing instrument can include an elongated tubular member that has a channel and a distal tip configured to penetrate and pierce tissue. The suture passer is loaded with a flexible construct in the form of a suture loop terminating in a single tail. The suture passing instrument can include a handle assembly located at the proximal end of the elongated tubular member. The tip is located at the distal end of the elongated tubular member. The handle assembly can house a mechanism for facilitating advancing and retracting the flexible construct.

In an embodiment, a suture passer instrument comprises: a hollow shaft having a longitudinal axis, a distal end, and a proximal end; a tip at the distal end of the shaft, the tip having an opening for a flexible construct to pass through and a pointed end for penetrating tissue (piercing through tissue); and a flexible construct in the form of a loop terminating in a single tail. The flexible construct is configured to slidably extend through the shaft and tip of the suture passer. In an embodiment, the suture passer instrument is a SutureLasso™ instrument and the flexible construct is a FiberStick™ Link. The FiberStick™ Link is provided with (i) a first portion (about 12 inches forming a tail) that is stiffened to allow convenient and easy advancement through the cannulation of the suture passer, alleviating the need for a monofilament suture or wire suture shuttle; and (ii) a second portion in the form of a continuous, flexible uninterrupted loop (terminating in the single tail).

Methods of suturing tissue are also disclosed. In an embodiment, tissue can be sutured by passing a tail of a flexible strand within a suture passing instrument; passing the suture passing instrument through tissue; subsequently, advancing the tail to allow the suture passing instrument to be removed; and passing the tail through the loop of the flexible strand to form a direct pass cinch (a continuous, uninterrupted loop of the flexible strand through and around the tissue).

An exemplary method of suturing tissue comprises: (i) passing a flexible construct formed of a flexible strand with a loop terminating in a single tail through the shaft of a suture passer; (ii) passing the suture passer through tissue; (iii) advancing the tail of the flexible construct through the tip of the suture passer and removing the suture passer; (iv) passing the single tail through the loop of the flexible construct and forming a direct pass cinch; and (v) pulling the single tail to complete the stitch through a single portal and without additional shuttling steps and instrumentation.

Referring now to the drawings, where like elements are designated by like reference numerals, FIGS. 1-5 illustrate suture passing instrument 10 and flexible construct 50 employed in an exemplary method of tissue repair 100 (direct pass cinch repair 100) of the present disclosure.

As shown in FIG. 1, suture passing instrument 10 (suture passer 10; instrument 10; surgical instrument 10) comprises an elongated tubular member or shaft 12 having a longitudinal axis 12a, a proximal end 11, a distal end 13 and an axial throughbore therein. Shaft 12 may be a tube or a narrow-diameter rod of dimensions that permit the tubular member to be introduced through an associated cannula (for example, an 8.25 cannula) in a minimally invasive procedure, such as arthroscopic or other endoscopic procedures, or into a body cavity, such as the abdominal cavity. Alternatively, shaft 12 may be an open U channel (and not a closed tube). Shaft 12 houses a suture passage that allows easy passage of a first portion of flexible construct 50.

Elongated tubular member 12 connects, and extends between, a handle assembly 40 and a tip 15 designed to pierce tissue. Tip 15 is provided with an opening 19 that allows a first portion of flexible construct 50 to pass and extend therethrough, as more clearly illustrated in FIG. 3, for example. Opening 19 is provided in a most distal end of tip 15 and communicates with the suture passage. Preferably, the opening 19 has the shape of a channel with a round cross-section to allow the suture (which may have a generally circular cross-section) to pass therethrough. As shown in FIG. 11, distal opening 19 allows suture 51 to exit in a direction about perpendicular to the longitudinal axis of the instrument.

Flexible construct 50 is provided with a first portion 51 terminating with a second portion 55 in the form of a continuous, flexible uninterrupted loop 55. In an exemplary embodiment, flexible construct 50 is a FiberStick™ Link 50 provided with a first portion 51 which is about 12 inches long forming a tail 51. Tail 51 is stiffened to allow convenient and easy advancement through the cannulation of the suture passer, alleviating the need for a monofilament suture or wire suture shuttle. The second portion 55 is in the form of a continuous, flexible uninterrupted loop 55 terminating in the single tail 51.

Figure 2:
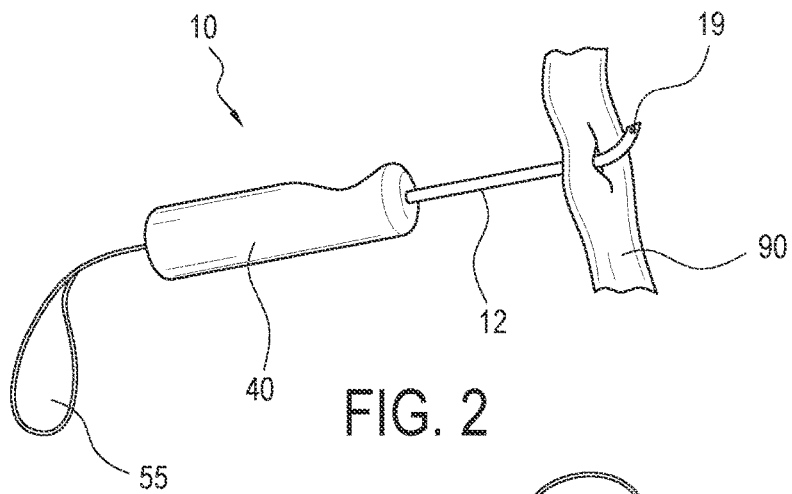
FIGS. 2-5 illustrate schematic subsequent steps of a tissue repair with the suture passing instrument and suturing construct of FIG. 1.
Figure 3:
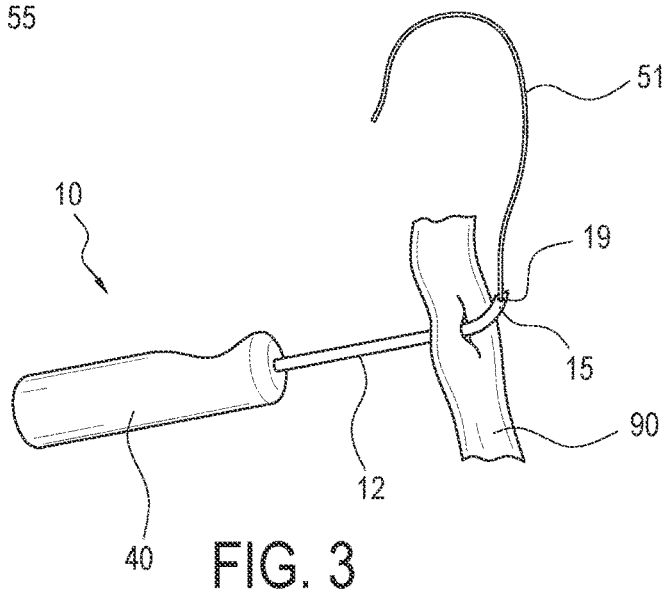

In use, FiberStick™ Link 50 is pushed forward toward opening 19 to exit the opening as shown in FIG. 3, for example. FIGS. 2 and 3 illustrate an exemplary flexible strand 50 (flexible material 50, suture construct 50, suturing construct 50, single tail/loop construct 50) loaded onto the tip 15 of the instrument 10. Flexible strand 50 has a first region 51 and a second region 55. In an embodiment, the first region 51 is a single end or single tail 51, and the second region 55 is a continuous, uninterrupted, flexible loop 55.

Flexible strand 50 is formed of a single strand of material that is looped/joined to form loop 55 and single tail 51. In an embodiment, flexible strand 50 has a length and two ends that form a loop 55 terminating in a single tail 51. In an embodiment, flexible strand 50 has one end that forms loop 55 and the other end forming single tail 51 (flexible end 51). Loop 55 may be a continuous, uninterrupted, flexible loop formed of a material such as suture. Loop 55 terminates in single flexible end or tail 51. In one embodiment, the perimeter of loop 55 may be fixed. In one embodiment, loop 55 and tail 51 may be formed of suture having a round cross-section. The suture may have the same or different diameters. Loop 55 may be formed by splicing the flexible strand through itself, or by other methods known in the art, such as fusion, gluing, bonding, joining, braiding, interlinking, etc.

Flexible strand 50 (suturing construct 50) may include a single filament, or fiber, or can include multiple continuous filaments, segments or regions of filaments that have different configurations (for example, different diameters and/or different compositions). The filament regions/segments may each be homogenous (i.e., formed of a same material) or may be a combination of homogenous and heterogenous (i.e., formed of a plurality of materials). Exemplary materials may include suture, silk, cotton, nylon, polypropylene, polyethylene, ultrahigh molecular weight polyethylene (UHMWPE), polyethylene terephthalate (PET), and polyesters and copolymers thereof, or combinations thereof.

In an embodiment, the flexible strand 50 is made of any known suture construct, such as multifilament, braided, knitted, woven suture, or including fibers of ultrahigh molecular weight polyethylene (UHMWPE) or the FiberWire® suture (disclosed in U.S. Pat. No. 6,716,234, the disclosure of which is hereby incorporated by reference in its entirety herein). The flexible strand may be also formed of suture tape, for example, Arthrex FiberTape®, which is a high strength suture tape that is braided and rectangular-like in cross section and as disclosed in U.S. Pat. No. 7,892,256, the disclosure of which is incorporated by reference in its entirety herein.

Flexible strand 50 may also include, and be manufactured with, any kind of material (suture, nylon, silk, UHMWPE, metal, bioabsorbable, etc.) that can allow the flexible strand to form a loop terminating in a single tail.

In an exemplary embodiment, flexible strand 50 is loaded onto the instrument 10 as shown in FIG. 2, i.e., with tail 51 passed/loaded through the cannulation of the shaft 12 and with loop 55 at the proximal end 11 of the instrument 10.

FIGS. 2-5 illustrate schematic steps of a method of tissue repair (e.g., tendon or ligament repair) with instrument 10 and exemplary flexible strand 50.

FIG. 2: instrument 10 loaded with flexible strand 50 is passed through tissue 90; instrument 10 pokes tissue 90.

FIG. 3: flexible strand 50 is advanced so that the tail 51 advances out of the opening 19 of the tip 15 and allows the instrument to be removed from the site.

Figure 4:
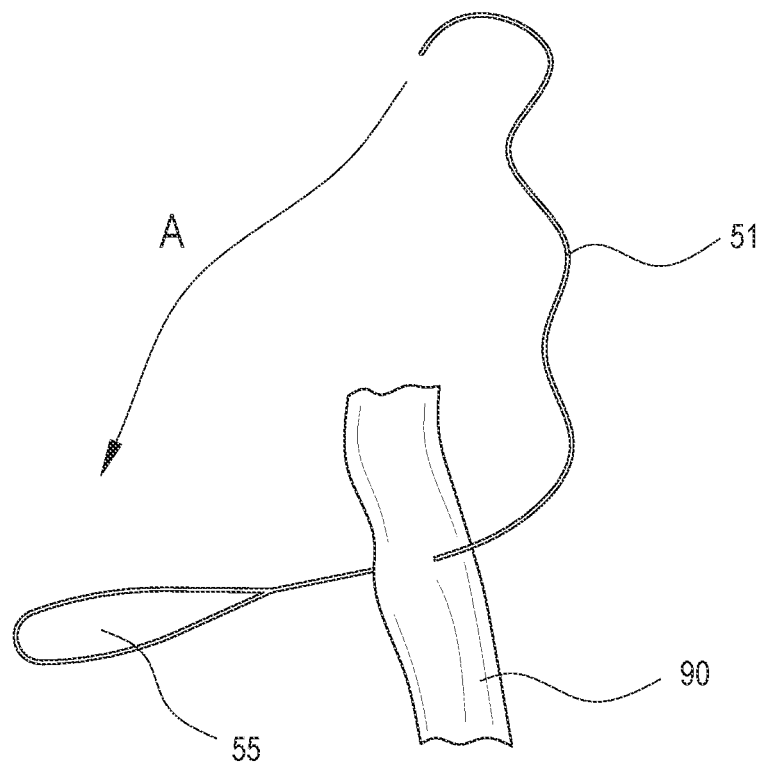

FIG. 4: once the instrument 10 has been removed, the tail 51 is passed through the loop 55 in the direction of arrow A.

Figure 5:
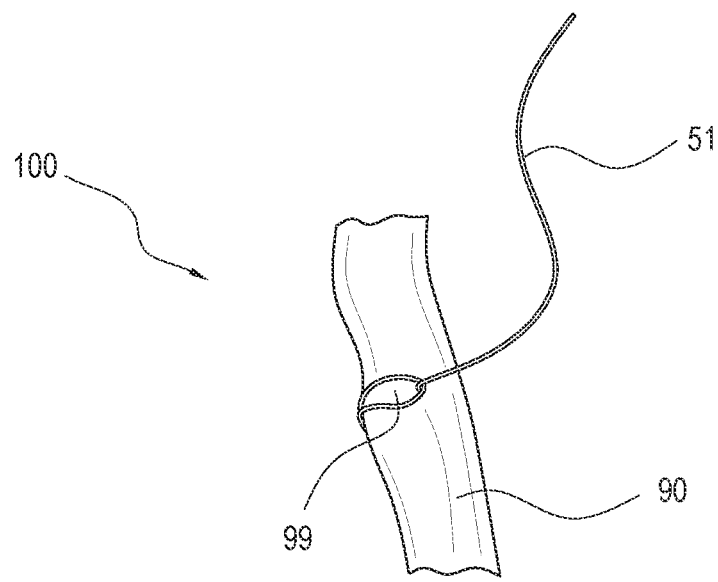

FIG. 5: cinch 99 is created by pulling the single tail 51 to be positioned around tissue 90 to complete a Loop 'N' Tack™ stitch 99 of repair 100 with a single portal and no shuttling steps.

Soft tissue 90 is luggage-tagged with looped suture 55 and the free end 51 of the suture 50. A Loop 'N' Tack™ knotless tenodesis technique is an all-arthroscopic technique using a FiberLink™ suture 50. The tendon/biceps is "luggage tagged" with the loop 55 of the FiberLink™ suture 50 and the free end 51 of the FiberLink™ suture 50 which pierces the biceps 90 and passes through it. A fixation device (for example, a SwiveLock® or PushLock® anchor) or similar structures may be employed to anchor the free suture end 51 and the biceps 90 intra-articularly at the top of the bicipital groove.

A direct pass cinch as disclosed herein may be employed in various surgical medical procedures for advancing a suture in proximity of a surgical site and forming a direct pass cinch. For example, instrument 10 and construct 50 may be employed in endoscopic surgery. The term "endoscopic surgery" refers to surgical procedures within a patient's body through small openings as opposed to conventional open surgery through large incisions.

According to an exemplary and illustrative embodiment only, a method of suturing a tissue using a direct pass cinch comprises: (i) loading a suture formed of a suture loop 55 terminating in a single tail 51 onto instrument 10; (ii) piercing tissue 90 with a tip of the instrument 10; (iii) advancing single tail 51 through the tip of the instrument; (iv) removing the instrument 10 from the surgical site; and (v) forming a direct pass cinch stitch around tissue 90 by passing single tail 51 through loop 55 and pulling the tail 51 through the suture loop 55 and through tissue 90.

Flexible strand 50 may be in the form of any elongated members, fibers, or materials, or combinations thereof. Flexible strand can include a single filament, or fiber, or can include multiple continuous filaments, segments or regions of filaments that have different configurations (for example, different diameters and/or different compositions). The filament regions/segments may each be homogenous (i.e., formed of a same material) or may be a combination of homogenous and heterogenous (i.e., formed of a plurality of materials). Exemplary materials may include suture, silk, cotton, nylon, polypropylene, polyethylene, ultrahigh molecular weight polyethylene (UHMWPE), polyethylene terephthalate (PET), and polyesters and copolymers thereof, or combinations thereof.

Flexible strand 50 may be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the suture, loop security, pliability, handleability or abrasion resistance, for example.

Flexible strand 50 may be also provided with tinted tracing strands, or otherwise contrast visually with other areas/regions of the construct, which remains a plain, solid color, or displays a different tracing pattern, for example. Various structural elements of flexible strand 50 such as loop 55 and/or tail 51 may be visually coded, making identification and handling of the suture loops and ends simpler. Easy identification of suture in situ is advantageous in surgical procedures.

The term "high strength suture" is defined as any elongated flexible member, the choice of material and size being dependent upon the particular application. For the purposes of illustration and without limitation, the term "suture" as used herein may be a cable, filament, thread, wire, fabric, or any other flexible member suitable for tissue fixation in the body.

The term "luggage tag stitch" is defined as any cinch or suture loop that is formed by the luggage tag technique.

What is claimed is:

1. A method of suturing tissue comprising:
    passing a flexible construct through a shaft of a suture passer;
    advancing the suture passer through an arthroscopic portal and through tissue to be sutured and piercing the tissue with a tip of the suture passer;
    advancing a tail at a distal end of the flexible construct through the shaft of the suture passer so that the tail exits a most distal end of the tip of the suture passer; and
    passing the tail through a continuous, uninterrupted loop on a proximal end of the flexible construct to form a cinch around and through the tissue, using the same arthroscopic portal and without shuttling devices.

2. The method of claim 1, wherein the flexible construct is a single strand with the tail at the distal end and the loop at the proximal end, opposite of the tail.

3. The method of claim 1, wherein the tissue is tendon or ligament.

4. A method of forming a direct pass cinch on tissue, comprising:
    inserting a tail at a distal end of a suturing construct through a shaft of a suture passer;
    advancing, through an arthroscopic portal, the suture passer with the suturing construct in the vicinity of a surgical site;
    piercing tissue at the surgical site with a tip of the suture passer;
    advancing the tail of the suturing construct through the shaft of the suture passer, so that the tail exits the tip of the suture passer;
    removing the suture passer from the surgical site;
    passing the tail of the suturing construct through a continuous, flexible, uninterrupted loop on the proximal end of the suturing construct; and
    pulling on the tail to form a cinch around and through the tissue, using the same arthroscopic portal and without any shuttling devices.

5. The method of claim 4, wherein the suturing construct is a single strand with the tail at the distal end and the loop at the proximal end, opposite of the tail.

6. The method of claim 4, wherein the suturing construct is formed of suture, silk, cotton, nylon, polypropylene, polyethylene, ultrahigh molecular weight polyethylene (UHMWPE), polyethylene terephthalate (PET), polyesters or copolymers, or combinations thereof.

7. The method of claim 4, wherein the continuous, flexible, uninterrupted loop has a fixed perimeter.

8. The method of claim 4, wherein the tail is stiffened.

9. The method of claim 4, wherein the tissue is soft tissue.

* * * * *